US012364689B2

(12) United States Patent
Morentin Gutierrez et al.

(10) Patent No.: US 12,364,689 B2
(45) Date of Patent: Jul. 22, 2025

(54) DOSAGE REGIMEN FOR THE TREATMENT OF CANCER

(71) Applicant: AstraZeneca AB, Södertälje (SE)

(72) Inventors: Pablo Morentin Gutierrez, Cambridge (GB); Camila De Almeida, Cambridge (GB); Eric Todd Gangl, Waltham, MA (US)

(73) Assignee: ASTRAZENECA AB, Södertälje (SE)

(*) Notice: Subject to any disclaimer, the term of this patent is extended or adjusted under 35 U.S.C. 154(b) by 149 days.

(21) Appl. No.: 18/152,255

(22) Filed: Jan. 10, 2023

(65) Prior Publication Data

US 2023/0248709 A1 Aug. 10, 2023

Related U.S. Application Data

(63) Continuation of application No. 17/237,112, filed on Apr. 22, 2021, now abandoned.

(60) Provisional application No. 63/014,914, filed on Apr. 24, 2020.

(51) Int. Cl.
*A61K 31/444* (2006.01)
*A61K 9/20* (2006.01)
*A61K 45/06* (2006.01)

(52) U.S. Cl.
CPC .............. *A61K 31/444* (2013.01); *A61K 9/20* (2013.01); *A61K 45/06* (2013.01)

(58) Field of Classification Search
CPC ......... A61K 31/444; A61K 9/20; A61K 45/06
USPC ...................................................... 514/210.2
See application file for complete search history.

(56) References Cited

U.S. PATENT DOCUMENTS

| | | | |
|---|---|---|---|
| 10,131,663 B2 | 11/2018 | Barlaam et al. | |
| 2009/0156557 A1 | 6/2009 | Brown et al. | |
| 2012/0157402 A1 | 6/2012 | Cao et al. | |
| 2014/0357661 A1 | 4/2014 | Akhtar et al. | |
| 2016/0175289 A1 | 6/2016 | Charles et al. | |
| 2018/0021316 A1 | 1/2018 | Barlaam et al. | |

FOREIGN PATENT DOCUMENTS

| | | |
|---|---|---|
| CN | 106518768 A | 3/2017 |
| CN | 107814798 A | 3/2018 |
| WO | 2002012242 A2 | 2/2002 |
| WO | 2006101434 A1 | 9/2006 |
| WO | 2006108948 A2 | 10/2006 |
| WO | 2007060198 A1 | 5/2007 |
| WO | 2010138695 A1 | 12/2010 |
| WO | 2010138758 A1 | 12/2010 |
| WO | 2011156518 A2 | 12/2011 |
| WO | 2011159769 A2 | 12/2011 |
| WO | 2013090829 A1 | 6/2013 |
| WO | 2013090836 A1 | 6/2013 |
| WO | 2014191726 A1 | 12/2014 |
| WO | 2014205136 A1 | 12/2014 |
| WO | 2014205138 A1 | 12/2014 |
| WO | 2015092634 A1 | 6/2015 |
| WO | 2016097071 A1 | 6/2016 |
| WO | 2016097072 A1 | 6/2016 |
| WO | 2016097073 A1 | 6/2016 |
| WO | 2016174551 A1 | 11/2016 |
| WO | 2016189011 A1 | 12/2016 |
| WO | 2016202161 A1 | 12/2016 |
| WO | 2017059139 A1 | 4/2017 |
| WO | 2017080338 A1 | 5/2017 |
| WO | 2017080966 A1 | 5/2017 |
| WO | 2017107754 A1 | 6/2017 |
| WO | 2017174757 A1 | 10/2017 |
| WO | 2017182493 A1 | 10/2017 |
| WO | 2017192991 A1 | 11/2017 |
| WO | 2018001232 A1 | 1/2018 |
| WO | 2018053354 A1 | 3/2018 |
| WO | 2018076090 A1 | 5/2018 |
| WO | 2018077630 A1 | 5/2018 |
| WO | 2018108671 A1 | 6/2018 |
| WO | 2018109607 A1 | 6/2018 |
| WO | 2018111315 A1 | 6/2018 |
| WO | 2018111707 A1 | 6/2018 |
| WO | 2018112379 A1 | 6/2018 |
| WO | 2018112382 A1 | 6/2018 |
| WO | 2018138293 A1 | 8/2018 |

OTHER PUBLICATIONS

Royce et al., "Everolimus in the Treatment of Metastatic Breast Cancer", Breast Cancer: Basic and Clinical Research, 2015, vol. 9, pp. 73-79.
Baird et al., "Abstract PS11-05: Updated data from SERENA-1: A Phase 1 dose escalation and expansion study of the next generation oral SERD AZD9833 as a monotherapy and in combination with Palbociclib, in women with ER-positive, HER2-negative advanced breast cancer", Journal of Cancer Research, Feb. 1, 2021.
Cancer Prevention Overview (PDQ)—National Cancer Institute, "What is prevention?", May 25, 2012.
Chesworth et al., "Tetrahydroisoquinolines as subtype selective estrogen agonists/antagonists", Bioorg. and Med. Chem. Lett, 2004, 14(11), 2729-2733.
Golub, Tr., "Molecular classification of cancer: class discovery and class prediction by gene expression monitoring." Science. Oct. 15, 1999;286(5439):531-7.
Gu et al., "Targeted therapy for breast cancer and molecular mechanisms of resistance to treatment", Current Opinion in Pharmacology, Nov. 22, 2016, pp. 97-103, vol. 31, Elsevier Science Publishers, NL.
Hamilton et al., "A phase I dose escalation and expansion study of the next generation oral SERD AZD9833 in women with ER-positive, HER2-negative advanced breast cancer", Journal of Clinical Oncology, May 20, 2020, 1024-1024.

(Continued)

*Primary Examiner* — Yevgeny Valenrod (57) ABSTRACT

The present specification relates to AZD9833 for use in the treatment of cancer and methods of treatment of cancer involving administration of AZD9833 wherein, in each case, the AZD9833 is administered orally once daily at a dose between 25 mg and 450 mg. AZD9833 may be administered alone or its use may be in combination with an additional anti-cancer agent such as a CDK inhibitor, everolimus or an AKT inhibitor.

13 Claims, 4 Drawing Sheets

(56) References Cited

OTHER PUBLICATIONS

International Search Report and Written Opinion for International Application No. PCT/EP2017/076191, dated Nov. 10, 2017.
Scott et al., "Discovery of AZD9833, a Potent and Orally Bioavailable Selective Estrogen Receptor Degrader and Antagonist", Journal of Medicinal Chemistry, Sep. 10, 2020, 63, 23, pp. 14530-14559.
Targeted Cancer Therapies Fact Sheet—National Cancer Institute, "What are targeted cancer therapies?", Dec. 8, 2015.

DOSAGE REGIMEN FOR THE TREATMENT OF CANCER

CROSS-REFERENCE TO RELATED APPLICATION

This application is a continuation of U.S. application Ser. No. 17/237,112, filed on Apr. 22, 2021, which claims the benefit under 35 U.S.C. § 119 (e) of U.S. Provisional Application No. 63/014,914, filed on Apr. 24, 2020. The above-listed applications are incorporated by reference herein in their entirety.

FIELD

The present specification relates to N-(1-(3-fluoropropyl)azetidin-3-yl)-6-((65,8R)-8-methyl-7-(2,2,2-trifluoroethyl)-6,7,8,9-tetrahydro-3H-pyrazolo[4,3-f] isoquinolin-6-yl)pyridin-3-amine (AZD9833, Compound (I) below) for use in the treatment of cancer, characterised in that the compound is for once daily oral administration in a specified dose. The specification also relates to methods of treatment involving once daily oral administration of AZD9833 in a specified dose to a patient in need thereof, the use of AZD9833 for the production of a medicament where the medicament is for once daily oral administration in a specified dose, pharmaceutical compositions comprising certain amounts of AZD9833 and kits of such pharmaceutical compositions.

(I)

BACKGROUND

Estrogen receptor alpha (ERα, ESR1, NR3A) and estrogen receptor beta (ERβ, ESR2, NR3b) are steroid hormone receptors which are members of the large nuclear receptor family. Structured similarly to all nuclear receptors, ERα is composed of six functional domains (named A-F) (Dahlman-Wright, et al., Pharmacol. Rev., 2006, 58:773-781) and is classified as a ligand-dependent transcription factor because after its association with the specific ligand, (the female sex steroid hormone 17b estradiol (E2)), the complex binds to genomic sequences, named Estrogen Receptor Elements (ERE) and interacts with co-regulators to modulate the transcription of target genes. The ERα gene is located on 6q25.1 and encodes a 595AA protein and multiple isoforms can be produced due to alternative splicing and translational start sites. In addition to the DNA binding domain (Domain C) and the ligand binding domain (Domain E) the receptor contains a N-terminal (A/B) domain, a hinge (D) domain that links the C and E domains and a C-terminal extension (F domain). While the C and E domains of ERα and ERβ are quite conserved (96% and 55% amino acid identity respectively) conservation of the A/B, D and F domains is poor (below 30% amino acid identity). Both receptors are involved in the regulation and development of the female reproductive tract and in addition play roles in the central nervous system, cardiovascular system and in bone metabolism. The genomic action of ERs occurs in the nucleus of the cell when the receptor binds EREs directly (direct activation or classical pathway) or indirectly (indirect activation or non-classical pathway). In the absence of ligand, ERs are associated with heat shock proteins, Hsp90 and Hsp70, and the associated chaperone machinery stabilizes the ligand binding domain (LBD) making it accessible to ligand. Liganded ER dissociates from the heat shock proteins leading to a conformational change in the receptor that allows dimerization, DNA binding, interaction with co-activators or co-repressors and modulation of target gene expression. In the non-classical pathway, AP-1 and Sp-1 are alternative regulatory DNA sequences used by both isoforms of the receptor to modulate gene expression. In this example, ER does not interact directly with DNA but through associations with other DNA bound transcription factors e.g. c-Jun or c-Fos (Kushner et al., Pure Applied Chemistry 2003, 75:1757-1769). The precise mechanism whereby ER affects gene transcription is poorly understood but appears to be mediated by numerous nuclear factors that are recruited by the DNA bound receptor. The recruitment of co-regulators is primarily mediated by two protein surfaces, AF2 and AF1 which are located in the E-domain and the A/B domain respectively. AF1 is regulated by growth factors and its activity depends on the cellular and promoter environment whereas AF2 is entirely dependent on ligand binding for activity. Although the two domains can act independently, maximal ER transcriptional activity is achieved through synergistic interactions via the two domains (Tzukerman, et al., Mol. Endocrinology, 1994, 8:21-30). Although ERs are considered transcription factors they can also act through non-genomic mechanisms as evidenced by rapid ER effects in tissues following E2 administration in a timescale that is considered too fast for a genomic action. It is still unclear if receptors responsible for the rapid actions of estrogen are the same nuclear ERs or distinct G-protein coupled steroid receptors (Warner, et al., Steroids 2006 71:91-95) but an increasing number of E2 induced pathways have been identified e.g. MAPK/ERK pathway and activation of endothelial nitric oxide synthase and PI3K/Akt pathway. In addition to ligand dependent pathways, ERα has been shown to have ligand independent activity through AF-1 which has been associated with stimulation of MAPK through growth factor signalling e.g. insulin like growth factor 1 (IGF-1) and epidermal growth factor (EGF). Activity of AF-1 is dependent on phosphorylation of Ser118 and an example of cross-talk between ER and growth factor signalling is the phosphorylation of Ser 118 by MAPK in response to growth factors such as IGF-1 and EGF (Kato, et al., Science, 1995, 270:1491-1494).

A large number of structurally distinct compounds have been shown to bind to ER. Some compounds such as endogenous ligand E2, act as receptor agonists whereas others competitively inhibit E2 binding and act as receptor antagonists. These compounds can be divided into 2 classes depending on their functional effects. Selective estrogen receptor modulators (SERMs) such as tamoxifen have the ability to act as both receptor agonists and antagonists depending on the cellular and promoter context as well as the ER isoform targeted. For example, tamoxifen acts as an antagonist in breast but acts as a partial agonist in bone, the cardiovascular system and uterus. All SERMs appear to act as AF2 antagonists and derive their partial agonist characteristics through AF1. A second group, fulvestrant being an example, are classified as full antagonists and are capable of blocking estrogen activity via the complete inhibition of AF1 and AF2 domains through induction of a unique conformation change in the ligand binding domain (LBD) on compound binding which results in complete abrogation of the interaction between helix 12 and the remainder of the LBD, blocking co-factor recruitment (Wakeling, et al., Cancer Res., 1991, 51:3867-3873; Pike, et al., Structure, 2001, 9:145-153).

Intracellular levels of ERα are downregulated in the presence of E2 through the ubiquitin/proteasome (Ub/26S) pathway. Polyubiquitinylation of liganded ER is catalysed by at least three enzymes; the ubiquitin-activating enzyme E1 activated ubiquitin is conjugated by E2 with lysine residues through an isopeptide bond by E3 ubiquitin ligase and polyubiquitinated ERx is then directed to the proteasome for degradation. Although ER-dependent transcription regulation and proteasome-mediated degradation of ER are linked (Lonard, et al., Mol. Cell, 2000 5:939-948), transcription in itself is not required for ERα degradation and assembly of the transcription initiation complex is sufficient to target ERα for nuclear proteasomal degradation. This E2 induced degradation process is believed to necessary for its ability to rapidly activate transcription in response to requirements for cell proliferation, differentiation and metabolism (Stenoien, et al., Mol. Cell Biol., 2001, 21:4404-4412). Fulvestrant is also classified as a selective estrogen receptor down-regulator (SERD), a subset of antagonists that can also induce rapid down-regulation of ERx via the 26S proteasomal pathway. In contrast a SERM such as tamoxifen can increase ERα levels although the effect on transcription is similar to that seen for a SERD.

Approximately 70% of breast cancers express ER and/or progesterone receptors implying the hormone dependence of these tumor cells for growth. Other cancers such as ovarian and endometrial are also thought to be dependent on ERα signalling for growth. Therapies for such patients can inhibit ER signalling either by antagonising ligand binding to ER e.g. tamoxifen which is used to treat early and advanced ER positive breast cancer in both pre- and post-menopausal setting; antagonising and down-regulating ERα e.g. fulvestrant which is used to treat breast cancer in women which have progressed despite therapy with tamoxifen or aromatase inhibitors; or blocking estrogen synthesis e.g. aromatase inhibitors which are used to treat early and advanced ER positive breast cancer. Although these therapies have had an enormously positive impact on breast cancer treatment, a considerable number of patients whose tumors express ER display de novo resistance to existing ER therapies or develop resistance to these therapies over time. Several distinct mechanisms have been described to explain resistance to first-time tamoxifen therapy which mainly involve the switch from tamoxifen acting as an antagonist to an agonist, either through the lower affinity of certain co-factors binding to the tamoxifen-ERα complex being off-set by over-expression of these co-factors, or through the formation of secondary sites that facilitate the interaction of the tamoxifen-ERα complex with co-factors that normally do not bind to the complex. Resistance could therefore arise as a result of the outgrowth of cells expressing specific co-factors that drive the tamoxifen-ERα activity. There is also the possibility that other growth factor signalling pathways directly activate the ER receptor or co-activators to drive cell proliferation independently of ligand signalling.

More recently, mutations in ESR1 have been identified as a possible resistance mechanism in metastatic ER-positive patient derived tumor samples and patient-derived xenograft models (PDX) at frequencies varying from 17-25%. These mutations are predominantly, but not exclusively, in the ligand-binding domain leading to mutated functional proteins; examples of the amino acid changes include Ser463Pro, Val543Glu, Leu536Arg, Tyr537Ser, Tyr537Asn and Asp538Gly, with changes at amino acid 537 and 538 constituting the majority of the changes currently described. These mutations have been undetected previously in the genomes from primary breast samples characterised in the Cancer Genome Atlas database. Of 390 primary breast cancer samples positive for ER expression not a single mutation was detected in ESR1 (Cancer Genome Atlas Network, 2012 Nature 490:61-70). The ligand binding domain mutations are thought to have developed as a resistance response to aromatase inhibitor endocrine therapies as these mutant receptors show basal transcriptional activity in the absence of estradiol. The crystal structure of ER, mutated at amino acids 537 and 538, showed that both mutants favoured the agonist conformation of ER by shifting the position of helix 12 to allow co-activator recruitment and thereby mimicking agonist activated wild type ER. Published data has shown that endocrine therapies such as tamoxifen and fulvestrant can still bind to ER mutant and inhibit transcriptional activation to some extent and that fulvestrant is capable of degrading Try537Ser but that higher doses may be needed for full receptor inhibition (Toy et al., Nat. Genetics 2013, 45:1439-1445; Robinson et al., Nat. Genetics 2013, 45:144601451; Li, S. et al. Cell Rep. 4, 1116-1130 (2013). It is therefore feasible that Compound (I) or pharmaceutically acceptable salts thereof (as described hereinafter) will be capable of down-regulating and antagonising mutant ER although it is not known at this stage whether ESR1 mutations are associated with an altered clinical outcome.

Regardless of which resistance mechanism or combination of mechanisms takes place, many are still reliant on ER-dependent activities and removal of the receptor through a SERD mechanism offers the best way of removing the ERα receptor from the cell. Fulvestrant is currently the only SERD approved for clinical use, yet despite its mechanistic properties, the pharmacological properties of the drug have limited its efficacy due to the current limitation of a 500 mg monthly dose which results in less than 50% turnover of the receptor in patient samples compared to the complete down-regulation of the receptor seen in in vitro breast cell line experiments (Wardell, et al., Biochem. Pharm., 2011, 82:122-130).

AZD9833, N-(1-(3-fluoropropyl) azetidin-3-yl)-6-((6S, 8R)-8-methyl-7-(2,2,2-trifluoroethyl)-6,7,8,9-tetrahydro-3H-pyrazolo[4,3-f] isoquinolin-6-yl) pyridin-3-amine, optionally provided as a pharmaceutically acceptable salt thereof, has been identified as a compound with the ability to act as a selective estrogen receptor down-regulator (SERD). AZD9833 is described as example 17 in WO2018/077630A1 wherein methods for the synthesis of the compound and its biological activity in in vitro and in vivo experiments are disclosed. Furthermore, in contrast to the fulvestrant, the only SERD currently approved for clinical use, that is administered by intramuscular injection, preclinical work indicated that AZD9833 has a physicochemical profile compatible with oral administration.

Given its favourable properties, it was envisaged that AZD9833 administered orally on a daily basis might achieve superior estrogen receptor degradation than that delivered by fulvestrant. As described for the first time herein, preliminary results from clinical trials on daily oral administration of AZD9833 has led to the discovery of a range of doses that in heavily pre-treated patients have elicited partial response as established according to the RECIST criteria (for example according to RECIST 1.1 criteria, see https://recist.eortc.org/; Eur. J. Cancer 2016, 62, Pages 132-137).

SUMMARY

It is an object of the present specification to provide an appropriate dose and dosing regimen for use of AZD9833 in the treatment of cancer, for example for use in the treatment of breast cancer.

In a first aspect of the present specification there is provided AZD9833 for use in the treatment of cancer where the AZD9833 is administered orally once daily at a dose between 25 mg and 450 mg.

In a second aspect of the present specification there is provided a method of treatment for cancer comprising administration of AZD9833 in a dose between 25 mg and 450 mg once daily to a patient in need thereof.

In a third aspect of the present specification there is provided the use of AZD9833 in the manufacture of a medicament for the treatment of cancer, where the AZD9833 is administered orally once daily at a dose between 25 mg and 450 mg.

In a fourth aspect of the present specification there is provided a pharmaceutical composition for once daily oral administration comprising between 25 mg and 450 mg of AZD9833 and a pharmaceutically acceptable excipient.

In a fifth aspect of the present specification there is provided a pharmaceutical composition for once daily oral administration comprising between 25 mg and 450 mg of AZD9833 and a pharmaceutically acceptable excipient for use in the treatment of cancer.

In a sixth aspect of the present specification there is provided a kit comprising a pharmaceutical composition comprising AZD9833 and at least one pharmaceutically acceptable excipient and instructions for the use of the pharmaceutical composition in the treatment of cancer, where the AZD9833 is for once daily administration at a dose between 25 mg and 450 mg.

FIGURES

So that the specification may be better understood, reference is made to the following figures.

DETAILED DESCRIPTION

The invention detailed in this specification should not be interpreted as being limited to any of the recited embodiments or examples. Other embodiments will be readily apparent to a reader skilled in the art.

"A" or "an" mean "at least one". In any embodiment where "a" or "an" are used to denote a given element, "a" or "an" may mean one. In any embodiment where "a" or "an" are used to denote a given element, "a" or "an" may mean 1, 2, 3, 4, 5, 6, 7, 8, 9 or 10.

When it is mentioned that "in some embodiments . . . " a certain feature may be present, the feature may be present in a suitable embodiment in any part of the specification, not just a suitable embodiment in the same section or textual region of the specification.

Claims are embodiments.

Therapeutic Use

In one embodiment there is provided AZD9833 for use in the treatment of cancer, where the AZD9833 is administered orally once daily at a dose between 25 mg and 450 mg.

In one embodiment there is provided AZD9833 for use in producing an anti-proliferative effect, where the AZD9833 is administered orally once daily at a dose between 25 mg and 450 mg.

In one embodiment there is provided AZD9833 for selectively inhibiting ERα, where the AZD9833 is administered orally once daily at a dose between 25 mg and 450 mg.

In one embodiment there is provided the use of AZD9833 in the manufacture of a medicament for the treatment of cancer, where the AZD9833 is administered orally once daily at a dose between 25 mg and 450 mg.

In one embodiment there is provided the use of AZD9833 in the manufacture of a medicament for producing an anti-proliferative effect, where the AZD9833 is administered orally once daily at a dose between 25 mg and 450 mg.

In one embodiment there is provided the use of AZD9833 in the manufacture of a medicament for selectively inhibiting ERα, where the AZD9833 is administered orally once daily at a dose between 25 mg and 450 mg.

In one embodiment there is provided a method of treating cancer in a human or animal patient in need of such treatment, comprising administering to the patient AZD9833 orally once daily at a dose between 25 mg and 450 mg.

In one embodiment there is provided a method of producing an anti-proliferative effect in a human or animal patient in need of such an effect, comprising administering to the patient AZD9833 orally once daily at a dose between 25 mg and 450 mg.

In one embodiment there is provided a method of selectively inhibiting ERα in a human or animal patient in need of such an effect, comprising administering to the patient AZD9833 orally once daily at a dose between 25 mg and 450 mg.

Compound

In some embodiments AZD9833 may be N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f] isoquinolin-6-yl) pyridin-3-amine or a pharmaceutically acceptable salt thereof. N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f] isoquinolin-6-yl) pyridin-3-amine has the structure of compound (I) above.

In some embodiments AZD9833 may be N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f] isoquinolin-6-yl) pyridin-3-amine in a salt-free form (for example in a neutral or zwitterionic form, or for example in a free base form).

In some embodiments AZD9833 may be a pharmaceutically acceptable salt of N-(1-(3-fluoropropyl) azetidin-3-yl)-

6-((6S,8R)-8-methyl-7-(2,2,2-trifluoroethyl)-6,7,8,9-tetrahydro-3H-pyrazolo[4,3-f] isoquinolin-6-yl) pyridin-3-amine.

The term "pharmaceutically acceptable" is used to specify that an object (for example a salt, dosage form or excipient) is suitable for use in patients. An example list of pharmaceutically acceptable salts can be found in the "Handbook of Pharmaceutical Salts: Properties, Selection and Use", P. H. Stahl and C. G. Wermuth, editors, Weinheim/Zurich: Wiley-VCH/VFICA, 2002 or subsequent editions.

A suitable pharmaceutically acceptable salt of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f] isoquinolin-6-yl) pyridin-3-amine is, for example, an acid-addition salt. An acid addition salt of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f] isoquinolin-6-yl) pyridin-3-amine may be formed by bringing the compound into contact with a suitable inorganic or organic acid under conditions known to the skilled person.

An acid addition salt may for example be formed using an inorganic acid selected from hydrochloric acid, hydrobromic acid, sulphuric acid and phosphoric acid. An acid addition salt may also be formed using an organic acid selected from acetic acid, adipic acid, benzene sulfonic acid, benzoic acid, cinnamic acid, citric acid, D,L-lactic acid, ethane disulfonic acid, ethane sulfonic acid, fumaric acid, hydrochloric acid, L-tartaric acid, maleic acid, malic acid, malonic acid, methane sulfonic acid, napadisylic acid, phosphoric acid, saccharin, succinic acid, sulfuric acid, p-toluene sulfonic acid, toluene sulfonic acid and trifluoroacetic acid.

A further suitable pharmaceutically acceptable salt of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f] isoquinolin-6-yl) pyridin-3-amine is, for example, a salt formed within the human or animal body after administration of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f] isoquinolin-6-yl) pyridin-3-amine to said human or animal body.

Dose Level

In some embodiments the dose of AZD9833 may be selected from 25 mg, 75 mg, 150 mg, 300 mg and 450 mg.

In some embodiments the dose of AZD9833 may be 25 mg.

In some embodiments the dose of AZD9833 may be 75 mg.

In some embodiments the dose of AZD9833 may be 150 mg.

In some embodiments the dose of AZD9833 may be 300 mg.

In some embodiments the dose of AZD9833 may be 450 mg.

In some embodiments the dose of AZD9833 may be an oral daily dose.

An "oral daily dose" is the amount of AZD9833 administered by mouth in a 24-hour period.

In some embodiments the AZD9833 may be administered as a single dose.

In some embodiments the AZD9833 may be administered as a divided dose.

A "divided dose" is one where the total dose (for example the oral daily dose) is administered in multiple (for example 1, 2, 3, 4 or 5) portions.

In some embodiments the AZD9833 may be administered as a single dose unit or as multiple dose units.

A "dose unit" is a discrete dosage form, for example a specified number (for example 1, 2, 3, 4 or 5) of tablets or capsules.

In some embodiments the AZD9833 may be administered as a single tablet.

In some embodiments the AZD9833 may be administered as a single tablet once daily.

In some embodiments the AZD9833 may be administered orally as a single tablet once daily.

For the avoidance of doubt, when a range of doses for AZD9833 is presented herein, for example, a dose between 25 mg and 450 mg, the range includes the doses at the endpoints of the range as well as doses falling in between those endpoints, i.e. 25 mg and 450 mg and quantities in between.

Cancer

"Cancer" is used synonymously with tumor and lesion in this specification. Cancer may include primary cancer as well as secondary cancers and metastases.

The "treatment of cancer", "treating cancer" and similar terms encompass treating an existing cancer and/or preventing cancer.

In some embodiments the treatment of cancer or treating cancer may mean treating and preventing cancer.

In some embodiments the treatment of cancer or treating cancer may mean treating cancer.

In some embodiments the treatment of cancer or treating cancer may mean preventing cancer.

In some embodiments cancer may be selected from breast cancer and gynaecological cancer.

"Gynaecological cancer" includes womb cancer, ovarian cancer, cervical cancer, vulva cancer and vaginal cancer.

In some embodiments cancer may be selected from breast cancer, womb cancer, ovarian cancer, cervical cancer, vulva cancer and vaginal cancer.

In some embodiments cancer may be ER-positive HER2-negative breast cancer.

"ER-positive HER2-negative breast cancer" comprises tumors with estrogen receptors (are ER-positive) that do not have high levels of the HER2 gene or the HER2 protein (are HER2-negative). ER-positive and HER2-negative status can be determined by methods known in the art, including the use of commercial kits.

In some embodiments breast cancer may be ER-positive breast cancer.

In some embodiments breast cancer may be HER2-negative breast cancer.

In some embodiments cancer may be ER-positive HER2-negative advanced breast cancer.

In some embodiments breast cancer may be ER-positive advanced breast cancer.

In some embodiments breast cancer may be HER2-negative advanced breast cancer.

Patient Selection

In some embodiments AZD9833 may be administered to a pre- or post-menopausal woman.

In some embodiments AZD9833 may be administered to a pre-menopausal woman.

In some embodiments AZD9833 may be administered to a post-menopausal woman.

In some embodiments AZD9833 may be administered to a pre- or post-menopausal woman whose cancer is ER-positive.

In some embodiments AZD9833 may be administered to a pre- or post-menopausal woman whose cancer is HER2-negative.

In some embodiments AZD9833 may be administered to a pre- or post-menopausal woman whose cancer is ER-positive and HER2-negative.

In some embodiments AZD9833 may be administered to a pre- or post-menopausal woman whose cancer has an ESR1 mutation.

In some embodiments AZD9833 may be administered to a pre- or post-menopausal woman whose cancer does not have an ESR1 mutation.

In some embodiments AZD9833 may be administered to a patient whose cancer has previously been treated with between 1 and 15 anti-cancer therapies.

In some embodiments AZD9833 may be administered to a patient whose cancer has previously been treated with between 1 and 10 anti-cancer therapies.

In some embodiments AZD9833 may be administered to a patient whose cancer has previously been treated with between 1 and 5 anti-cancer therapies.

In some embodiments AZD9833 may be administered to a patient whose cancer has previously been treated with between 5 and 10 anti-cancer therapies.

Where a patient has "previously been treated", this refers to any treatment administered to the patient prior to them being dosed with AZD9833. Previous treatment does not imply that the therapy in question was successful or curative, only that a patient received treatment with the therapy (for example, as a result of being prescribed the therapy by a suitably qualified healthcare professional).

"Anti-cancer therapies" include medicaments, drugs, compounds or other medical approaches (for example treatments using a patient's own immunological agents) aimed at the treatment of cancer. Example anti-cancer therapies are endocrine therapies and chemotherapies.

"Endocrine therapies" are those which work by modulating a patient's hormonal pathways. Examples include estrogen inhibitors (such as tamoxifen or fulvestrant), aromatase inhibitors (such as letrozole, anastrozole, vorazole or exemestane), progestogens (such as megestrol acetate) and luteinising hormone blockers (such as leuprolide or goserelin).

"Chemotherapies" are cancer therapies which are not endocrine therapies. They include for example:
i. Traditional antiproliferative/antineoplastic drugs and combinations thereof, including alkylating agents (for example cisplatin, oxaliplatin, carboplatin, cyclophosphamide, nitrogen mustard, melphalan, chlorambucil, busulphan, temozolomide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and tenoposide, amsacrine, topotecan and camptothecin);
ii. Inhibitors of growth factor function and their downstream signalling pathways, including Ab modulators of any growth factor or growth factor receptor targets, as for example reviewed by Stern et al. Critical Reviews in Oncology/Haematology, 2005, 54, pp11-29; small molecule inhibitors of such targets, for example kinase inhibitors. Specific examples include the anti erbB2 antibodies trastuzumab [Herceptin™] and pertuzumab [Perjeta™], the HER-2 directed antibody-drug conjugates trastuzumab deruxtecan [Enhertu™] and trastuzumab emtansine [Kadcyla™], the anti-EGFR antibody panitumumab, the anti EGFR antibody cetuximab (Erbitux, C225) and tyrosine kinase inhibitors including inhibitors of the erbB receptor family, such as epidermal growth factor family receptor (EGFR/erbB1), tyrosine kinase inhibitors such as gefitinib, osimertinib or erlotinib, erbB2 tyrosine kinase inhibitors such as lapatinib, and mixed erb1/2 inhibitors such as afatinib. Other example classes of growth factors and their receptor modulators include for example inhibitors of the hepatocyte growth factor family or their receptors (including c-met and ron); inhibitors of the insulin and insulin growth factor family or their receptors (IGFR, IR), inhibitors of the platelet-derived growth factor (PDGFR) family or their receptors and inhibitors of signalling mediated by other receptor tyrosine kinases such as c-kit, AnLK, and CSF-1R; modulators which target signalling proteins in the PI3-kinase signalling pathway, for example, inhibitors of PI3-kinase isoforms such as PI3K-α, PI3K-β. PI3K-γ and PI3K-δ and ser/thr kinases such as AKT (such as capivasertib, afuresertib, miransertib, ARQ751, ipataserib, MK-2206 or perifosine), mTOR (such as AZD2014 or everolimus), PDK, SGK, PI4K or PIP5K; inhibitors of serine/threonine kinases not listed above, for example raf inhibitors such as vemurafenib, MEK inhibitors such as selumetinib (AZD6244), Abl inhibitors such as imatinib or nilotinib, Btk inhibitors such as ibrutinib, acalabrutinib, and zanubrutinib, Syk inhibitors such as fostamatinib, aurora kinase inhibitors (for example AZD1152), inhibitors of other ser/thr kinases such as JAKs, STATs and IRAK4, and cyclin dependent kinase inhibitors for example inhibitors of CDK1, CDK4, CDK6, CDK7, CDK9 and CDK4/6 (such as palbociclib, ribociclib, abemaciclib, lerociclib and trilaciclib);
iii. Modulators of DNA damage signalling pathways, for example PARP inhibitors (e.g. olaparib, rucaparib, niraparib and talazoparib), ATR inhibitors (such as AZD6738) or ATM inhibitors;
iv. Modulators of apoptotic and cell death pathways such as BCl family modulators (e.g. ABT-263/Navitoclax, ABT-199);
v. Antiangiogenic agents such as those which inhibit the effects of vascular endothelial growth factor, for example the anti-vascular endothelial cell growth factor antibody bevacizumab (Avastin™) or a VEGF receptor tyrosine kinase inhibitor such as sorafenib, axitinib, pazopanib, sunitinib or vandetanib (and compounds that work by other mechanisms (for example linomide, inhibitors of integrin function and angiostatin);
vi. Vascular damaging agents, such as Combretastatin A4;
vii. Anti-invasion agents, for example c-Src kinase family inhibitors like (dasatinib, J. Med. Chem., 2004, 47, 6658-6661) and bosutinib (SKI-606), and metalloproteinase inhibitors like marimastat, inhibitors of urokinase plasminogen activator receptor function or antibodies to heparanase);
viii. Immunotherapy, including for example ex vivo and in vivo approaches to increase the immunogenicity of patient tumor cells, such as transfection with cytokines such as interleukin 2, interleukin 4 or granulocyte macrophage colony stimulating factor, approaches to decrease T-cell anergy, approaches using transfected immune cells such as cytokine transfected dendritic cells, approaches using cytokine transfected tumor cell lines and approaches using anti idiotypic antibodies. Specific examples include monoclonal antibodies targeting PD-1 (e.g. pembrolizumab, nivolumab, cemiplimab), PD-L1 (e.g. durvalumab, atezolizumab or avelumab) or CTLA4 (e.g. ipilimumab and tremelimumab);

ix. Antisense or RNAi based therapies, for example those which are directed to the targets listed in this specification; and x. Gene therapy approaches, including for example approaches to replace aberrant genes such as aberrant p53 or aberrant BRCA1 or BRCA2, GDEPT (gene directed enzyme pro drug therapy), approaches such as those using cytosine deaminase, thymidine kinase or a bacterial nitro reductase enzyme and approaches to increase patient tolerance to chemotherapy or radiotherapy such as multi drug resistance gene therapy.

In some embodiments AZD9833 may be administered to a patient whose cancer has previously been treated with ≥1 endocrine therapy and ≤2 chemotherapies.

In some embodiments AZD9833 may be administered to a patient whose cancer has previously been treated with >1 endocrine therapy and ≤2 chemotherapies for ER-positive HER2-negative breast cancer.

"Chemotherapies for ER-positive HER2-negative breast cancer" may include any anti-cancer regimen(s) comprising at least one cytotoxic agent given for 21 days or longer.

In some embodiments AZD9833 may be administered to a patient whose cancer has previously been treated with >1 endocrine therapy and ≤2 chemotherapies for ER-positive HER2-negative advanced breast cancer.

In some embodiments the >1 endocrine therapy may be selected from an estrogen inhibitor, an aromatase inhibitor, a progestogen and a luteinising hormone blocker.

In some embodiments the >1 endocrine therapy may be selected from tamoxifen, toremifene, raloxifene, droloxifene, idoxifene, fulvestrant, letrozole, anastrozole, vorazole, exemestane, megestrol acetate, leuprolide and goserelin.

In some embodiments the ≤2 chemotherapies may be selected from a CDK inhibitor (such as a CD4, CDK6, or CDK4/CDK6 dual inhibitor) and an mTOR inhibitor.

In some embodiments the ≤2 chemotherapies may be selected from palbociclib, ribociclib, abemaciclib, trilaciclib, lerociclib and everolimus.

In some embodiments AZD9833 may be administered to a patient whose cancer is resistant to aromatase inhibitors.

In some embodiments AZD9833 may be administered to a patient whose cancer is resistant to non-steroidal aromatase inhibitors.

In some embodiments AZD9833 may be administered to a patient whose cancer is resistant to an aromatase inhibitor selected from letrozole and anastrozole.

When a patient's cancer is "resistant" (or refractory) to a particular drug or therapy, the cancer no longer responds sufficiently to treatment for it to be considered a suitable medical option going forward, such that an attending physician recommends a different therapeutic approach.

In some embodiments AZD9833 may be administered to a patient whose cancer is resistant to tamoxifen.

In some embodiments AZD9833 may be administered to a patient whose cancer is resistant to fulvestrant.

In some embodiments AZD9833 may be administered to a patient whose cancer is resistant to CDK inhibitors.

Pharmacokinetic and Pharmacodynamic Properties

In one embodiment there is provided AZD9833 for use in the treatment of cancer, where the AZD9833 is administered orally once daily at a dose between 25 mg and 450 mg and achieves a mean peak blood plasma concentration in a cancer patient of between 10 and 1000 ng/ml.

The "peak mean blood plasma concentration" refers to the maximum amount of AZD9833 achieved in a patient's plasma following treatment.

In one embodiment there is provided AZD9833 for use in the treatment of cancer, where the AZD9833 is administered orally once daily at a dose between 25 mg and 450 mg and achieves a median terminal half-life of between 8 h and 14 h in a cancer patient.

In one embodiment there is provided AZD9833 for use in the treatment of cancer, where the AZD9833 is administered orally once daily at a dose between 25 mg and 450 mg and achieves a median terminal half-life of 12 h in a cancer patient.

The "median terminal half-life" is the median time for a patient's drug blood plasma concentration to halve after reaching pseudo-equilibrium.

Clinical Properties

In one embodiment there is provided AZD9833 for use in the treatment of cancer, where the AZD9833 is administered orally once daily at a dose between 25 mg and 450 mg and achieves an objective response rate between 10% and 20%.

"Objective response rate" is the percentage of patients with measurable disease at baseline and who have a date of first dose of >17 weeks or a date of post-treatment scan of >15 weeks that indicates a confirmed response as measured by the RECIST criteria.

In one embodiment there is provided AZD9833 for use in the treatment of cancer, where the AZD9833 is administered orally once daily at a dose between 25 mg and 450 mg and achieves a clinical benefit rate between 25% and 100%.

"Clinical benefit rate" is the percentage of patients who have a date of first dose of ≥25 weeks or a date of post-treatment scan of >23 weeks that indicates a confirmed response or stable disease as measured by the RECIST criteria for >23 weeks post treatment.

In one embodiment there is provided AZD9833 for use in the treatment of cancer, where the AZD9833 is administered orally once daily at a dose between 25 mg and 450 mg and achieves a clinical benefit rate greater than 25%.

In one embodiment there is provided AZD9833 for use in the treatment of cancer, where the AZD9833 is administered orally once daily at a dose between 25 mg and 450 mg and achieves a clinical benefit rate between 25% and 90%.

In one embodiment there is provided AZD9833 for use in the treatment of cancer, where the AZD9833 is administered orally once daily at a dose between 25 mg and 450 mg and achieves a clinical benefit rate between 25% and 80%.

In one embodiment there is provided AZD9833 for use in the treatment of cancer, where the AZD9833 is administered orally once daily at a dose between 25 mg and 450 mg and achieves a clinical benefit rate between 25% and 75%.

In one embodiment there is provided AZD9833 for use in the treatment of cancer, where the AZD9833 is administered orally once daily at a dose between 25 mg and 450 mg and does not cause any serious side-effects in a cancer patient.

In some embodiments serious side-effects may be defined as grade 4 or 5 adverse events.

"Grade 4 or 5 adverse events" can be classified according to the common terminology criteria for adverse events (CTCAE).

Combination Treatment

In one embodiment there is provided AZD9833 for use in the treatment of cancer, where the AZD9833 is administered orally once daily at a dose between 25 mg and 450 mg in combination with a further anti-cancer therapy.

When a drug is administered "in combination" with AZD9833, the combination may comprise the separate, sequential, or simultaneous administration of the drugs. Where treatment is separate and/or sequential, the interval between the dose of AZD9833 and the dose of the further anti-cancer therapy may be chosen to ensure the production of a combined therapeutic effect.

In some embodiments the administration of the AZD9833 and a further anti-cancer therapy is separate.

In some embodiments the administration of the AZD9833 and a further anti-cancer therapy is sequential.

In some embodiments the administration of the AZD9833 and a further anti-cancer therapy is separate and sequential.

In some embodiments the further anti-cancer therapy may be a CDK inhibitor.

In some embodiments the further anti-cancer therapy may be a CDK4 inhibitor.

In some embodiments the further anti-cancer therapy may be a CDK6 inhibitor.

In some embodiments the further anti-cancer therapy may be a dual CDK4/CDK6 inhibitor.

In some embodiments the further anti-cancer therapy may be a CDK inhibitor selected from palbociclib, ribociclib, abemaciclib, lerociclib or trilaciclib.

In some embodiments the further anti-cancer therapy may be palbociclib.

In some embodiments the further anti-cancer therapy may be an mTOR inhibitor.

In some embodiments the further anti-cancer therapy may be an mTOR inhibitor selected from sirolimus, deforolimus, everolimus and temsirolimus.

In some embodiments the further anti-cancer therapy may be everolimus.

In some embodiments the further anti-cancer therapy may be everolimus which is administered orally once daily at a dose of up to 10 mg.

In some embodiments the further anti-cancer therapy may be selected from palbociclib, ribociclib, abemaciclib, lerociclib, trilaciclib and everolimus.

In some embodiments the further anti-cancer therapy may be selected from palbociclib, ribociclib, abemaciclib, lerociclib and trilaciclib.

In some embodiments the further anti-cancer therapy may be an AKT inhibitor.

In some embodiments the further anti-cancer therapy may be selected from capivasertib, afuresertib, miransertib, ARQ751, ipataserib, MK-2206 or perifosine.

Compositions

In one embodiment there is provided a composition for once daily oral administration comprising between 25 mg and 450 mg of AZD9833 and a pharmaceutically acceptable excipient.

In some embodiments pharmaceutically acceptable excipients may be selected from inert diluents (for example microcrystalline cellulose or dicalcium phosphate anhydrous), granulating agents, disintegrating agents (for example sodium starch glycolate), binding agents, lubricating agents (for example magnesium stearate), preservative agents, antioxidants and chelating agents.

In some embodiments the composition for once daily oral administration comprises between 25 mg and 450 mg of AZD9833, for example 25 mg, 75 mg or 100 mg of AZD9833, and at least one diluent selected from microcrystalline cellulose (MCC), dicalcium phosphate anhydrous (DCPA), mannitol, lactose, dicalcium phosphate, calcium sulfate dihydrate, tribasic calcium phosphate, dibasic calcium phosphates dihydrate, silicified microcrystalline cellulose, their co-processed combinations, polydextrose, trehalose, sucrose, glucose, cyclodextrin and hydroxypropyl cellulose.

The composition for once daily oral administration may further comprise at least one disintegrant selected from croscarmellose sodium, crospovidone, sodium starch glycolate (SSG) and low substituted hydroxypropyl cellulose (L-HPC).

The composition for once daily oral administration may further comprise at least one lubricant selected from magnesium stearate, calcium stearate, zinc stearate, sodium stearyl fumarate, glyceryl behenate and stearic acid.

Dosage Forms

In one embodiment there is provided a pharmaceutical composition comprising between 25 mg and 450 mg of AZD9833 and a pharmaceutically acceptable excipient in the form of a tablet or a capsule for once daily oral administration.

Tablet formulations may be uncoated or coated either to modify their disintegration and the subsequent absorption of the active ingredient within the gastrointestinal tract, or to improve their stability and/or appearance, in either case, using conventional coating agents and procedures known in the art. For example, tablet formulations may be treated such that they release active ingredients immediately.

In one embodiment there is provided a pharmaceutical composition comprising between 25 mg and 450 mg of AZD9833, for example between 25 and 100 mg of AZD9833, and a pharmaceutically acceptable excipient, which composition is an immediate release composition.

In one embodiment there is provided a pharmaceutical composition comprising between 25 mg and 450 mg of AZD9833, for example between 25 and 100 mg of AZD9833, and a pharmaceutically acceptable excipient in the form of a single tablet for once daily oral administration.

As well as tablets, compositions for oral use may alternatively be in the form of hard gelatine capsules in which the active ingredient is mixed with an inert solid diluent, or as soft gelatine capsules in which the active ingredient is mixed with water or an oil.

In one embodiment there is provided a pharmaceutical composition comprising between 25 mg and 450 mg of AZD9833, for example between 25 and 100 mg of AZD9833, and a pharmaceutically acceptable excipient in the form of a single capsule for once daily oral administration.

In one embodiment there is provided the use of a pharmaceutical composition comprising between 25 mg and 450 mg of AZD9833, for example between 25 and 100 mg of AZD9833, and a pharmaceutically acceptable excipient in the treatment of cancer, where the pharmaceutical composition is administered once daily.

Kits

In one embodiment there is provided a kit comprising a pharmaceutical composition comprising AZD9833 and at least one pharmaceutically acceptable excipient and instructions for the use of the pharmaceutical composition in the treatment of cancer, where the AZD9833 is for once daily administration at a dose between 25 mg and 450 mg.

In one embodiment there is provided a kit comprising:
a pharmaceutical composition comprising AZD9833 and at least one pharmaceutically acceptable excipient;

an additional anti-cancer agent for administration in combination with AZD9833; and instructions for the use of the pharmaceutical composition in the treatment of cancer, where the AZD9833 is for once daily administration at a dose between 25 mg and 450 mg.

In one embodiment there is provided a kit comprising:

a pharmaceutical composition comprising AZD9833 and at least one pharmaceutically acceptable excipient;

an additional anti-cancer agent for administration in combination with AZD9833; and instructions for the use of the pharmaceutical composition in the treatment of cancer, where the AZD9833 is for once daily administration at a dose between 25 mg and 450 mg.

In one embodiment there is provided a kit comprising:

a pharmaceutical composition comprising AZD9833 and at least one pharmaceutically acceptable excipient;

an additional anti-cancer agent selected from palbociclib, ribociclib, abemaciclib or trilaciclib for administration in combination with AZD9833; and instructions for the use of the pharmaceutical composition in the treatment of cancer, where the AZD9833 is for once daily administration at a dose between 25 mg and 450 mg.

EXAMPLES

Clinical Trial Protocol

Introduction: To determine the optimal dosing regimen for AZD9833 Phase 1 dose-escalation and expansion in patients with ER positive, HER2 negative advanced breast cancer was carried out according to the following basic protocol.

Rationale: AZD9833 has the potential to provide superior clinical benefit to existing endocrine therapies through enhanced bioavailability (compared to fulvestrant, which is administered intramuscularly) and target (estrogen receptor) engagement and modulation in patients with estrogen receptor positive (ER+) breast cancer. The study's primary objective is to determine the safety and tolerability of AZD9833 in women with ER+human epidermal growth factor receptor 2 negative (HER2-) advanced breast cancer. In addition, the pharmacokinetics and preliminary anti-tumour activity of AZD9833 will be investigated.

Primary Objectives and Endpoints:

TABLE 1

| Primary/Safety Objective | Primary Endpoints/Variables |
|---|---|
| To investigate the safety and tolerability of AZD9833 in women with estrogen receptor positive (ER+) human epidermal growth factor receptor 2 negative (HER2−) advanced breast cancer to define the doses and schedules for further clinical evaluation of AZD9833 as a monotherapy. | Dose-limiting toxicities (DLTs). Adverse events (AEs)/serious adverse events (SAEs). Vital signs. Clinical chemistry/haematology parameters. Triplicate electrocardiograms (ECGs) |

Secondary Objectives and Endpoints:

TABLE 2

| Secondary Objective | Primary Endpoints/Variables |
|---|---|
| To assess the anti-tumour activity and efficacy of AZD9833 as a monotherapy. | According to the Response Evaluation Criteria in Solid Tumour (RECIST) 1.1 by investigator assessment: Objective response rate (ORR) Duration of response (DoR) Clinical benefit rate at 24 weeks (CBR 24weeks) Percentage change in tumour size Progression-free survival (PFS). |
| To characterise the single- and multiple-dose pharmacokinetics of AZD9833. | Plasma and urine AZD9833 concentrations and derived pharmacokinetic parameters. |
| To investigate AZD9833 activity in tumour cells. | Assessment of biomarker changes, which include expression levels of estrogen receptor (ER), progesterone receptor (PgR) and Ki67 protein. |

Exploratory Objectives and Endpoints:

TABLE 3

| Secondary Objective | Primary Endpoints/Variables |
|---|---|
| To investigate AZD9833 activity in tumour, circulating tumour cells (CTCs), and blood, including plasma circulating tumour DNA (ctDNA). | Assessment of exploratory biomarker changes, which may include but are not limited to expression levels of estrogen receptor-regulated gene expression, and gene mutational status. |
| To investigate predictive markers of response and/or acquired resistance to AZD9833 in tumour, blood, and plasma ctDNA. | Mutational status of cancer-associated genes in tumour and ctDNA. Assessment of exploratory blood borne biomarkers, including but not limited to gene expression. |
| To perform future exploratory research of biomarkers that may influence development of breast cancer and/or response to treatment. | Exploratory tumour and circulating biomarkers. |
| To collect and store DNA according to each country's local and ethical procedures for future exploratory research into genes/genetic variation that may influence response to treatment. | Possible future genetic research. Results may be reported outside this study's CSR. |
| To investigate any change in 4β-hydroxycholesterol/cholesterol ratio as a marker of cytochrome P450 3A4 (CYP3A4) induction by AZD9833. | Changes in the 4β-hydroxycholesterol/cholesterol ratio vs baseline. |
| To investigate any change in 4β-hydroxycholesterol/cholesterol ratio as a marker of cytochrome P450 3A4 (CYP3A4) induction by AZD9833. | Changes in the 4β-hydroxycholesterol/cholesterol ratio vs baseline. |

TABLE 3-continued

| Secondary Objective | Primary Endpoints/Variables |
|---|---|
| To investigate the effect of AZD9833 on ECG and cardiovascular parameters. | Exploratory assessment of blood pressure, echocardiogram and ECG data, the latter to include both triplicate and continuously acquired, and of methodologies to calculate QTc |

Overall Design: This is a multicentre dose escalation and expansion, first-in-human study designed to evaluate the safety and tolerability of AZD9833 alone (Parts A and B) in women with endocrine-resistant ER+HER2-breast cancer that is not amenable to treatment with curative intent.

Figure 1:
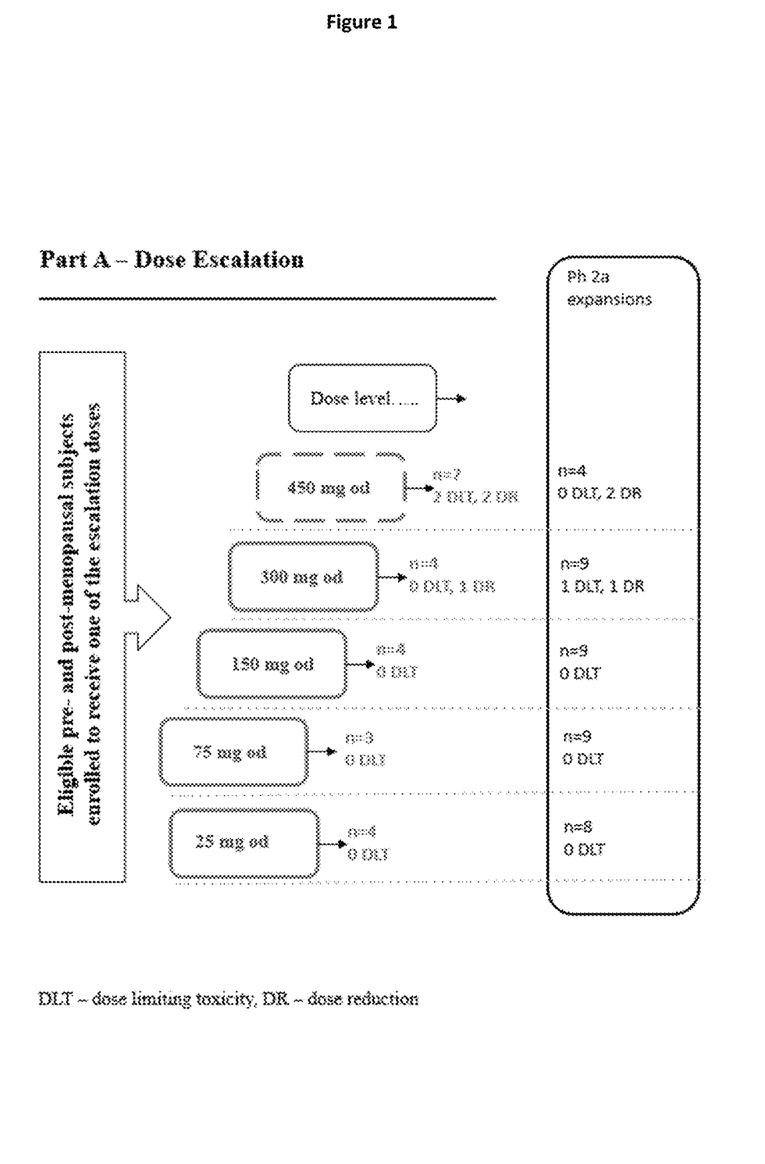
FIG. 1: Schematic of the dose-escalation phase of a phase I clinical trial in heavily pre-treated patients breast cancer patients suitable to demonstrate the benefits of AZD9833 treatments across the dose range.
Figure 2:
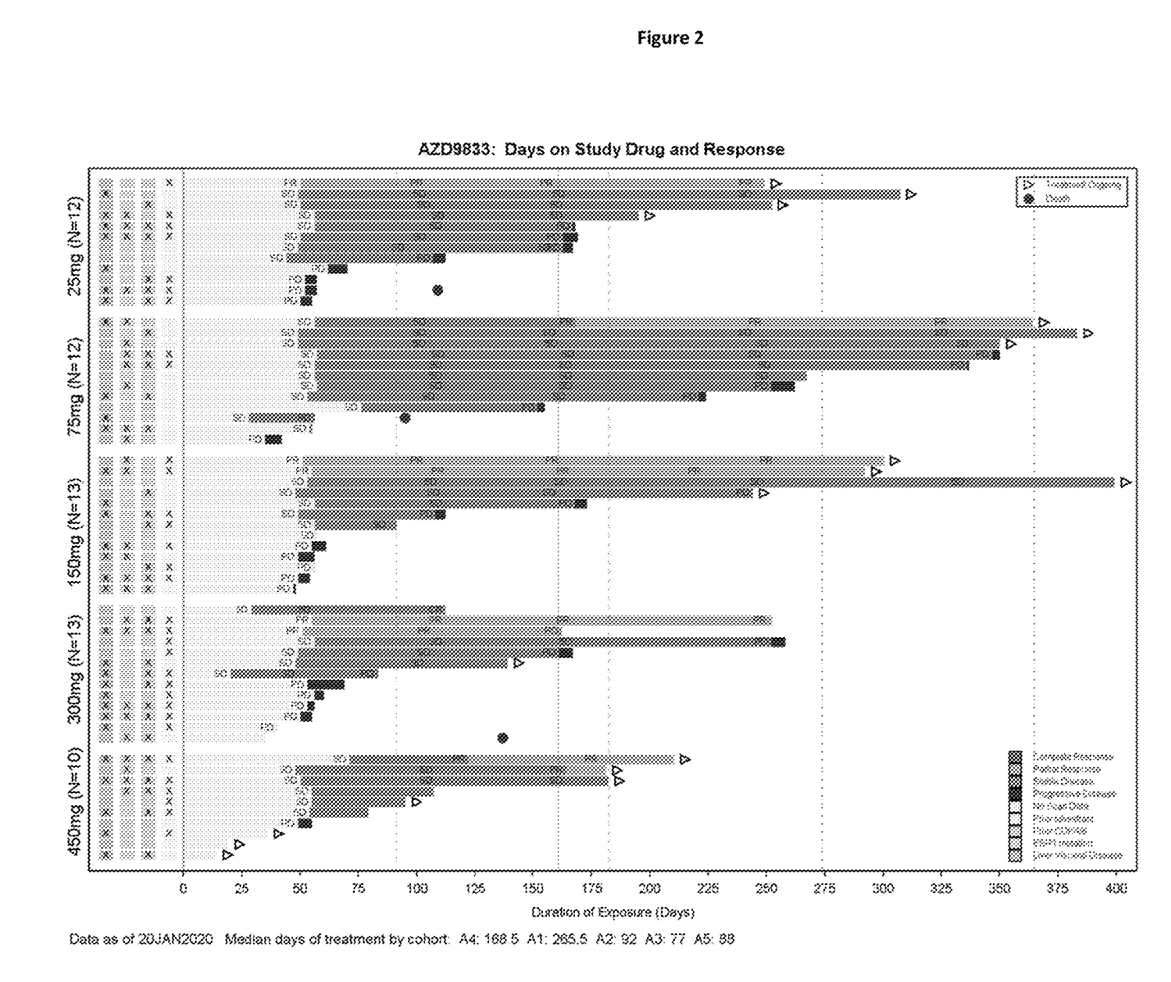
FIG. 2: Swimmer plot of patient responses after treatment with ascending doses of AZD9833.
Figure 3:
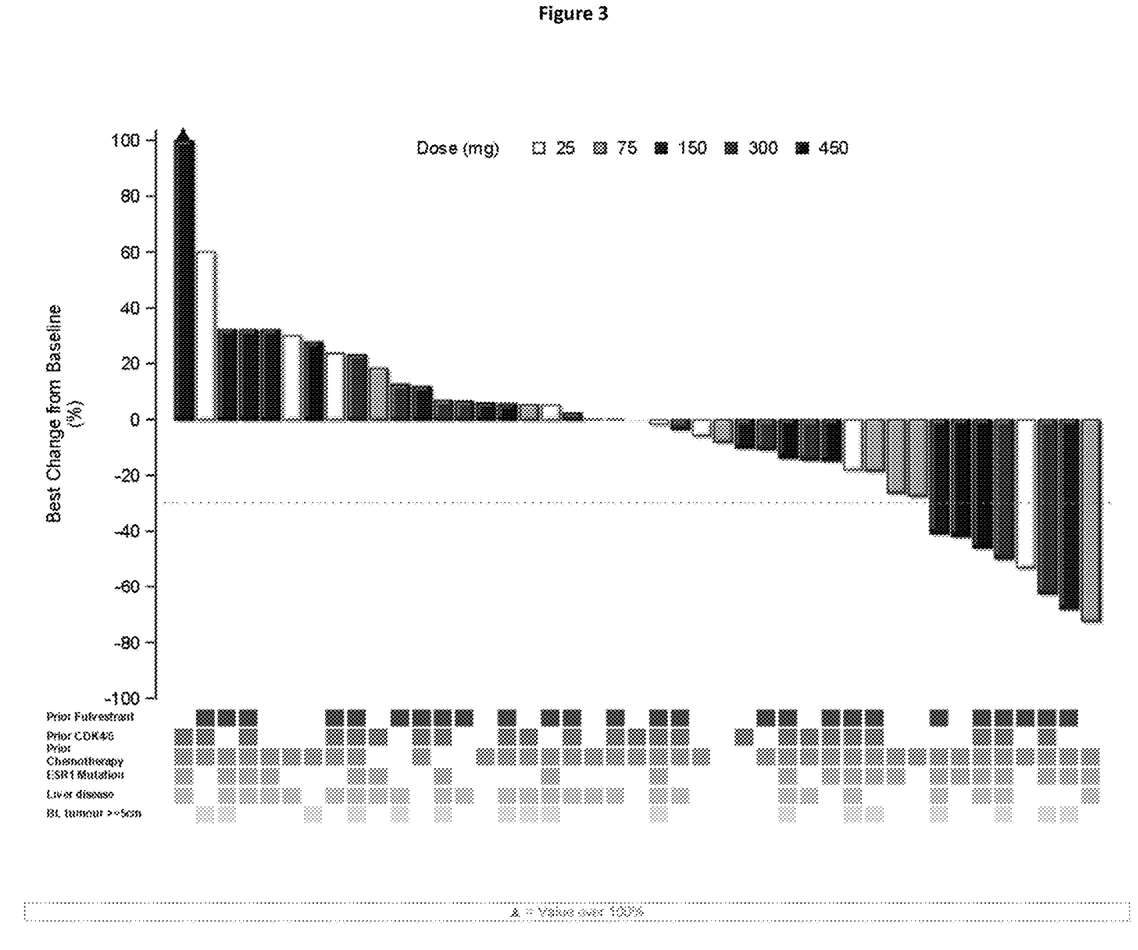
FIG. 3: Composite waterfall plot showing best change in tumor size from baseline in patients treated with varying doses of AZD9833.
Figure 4:
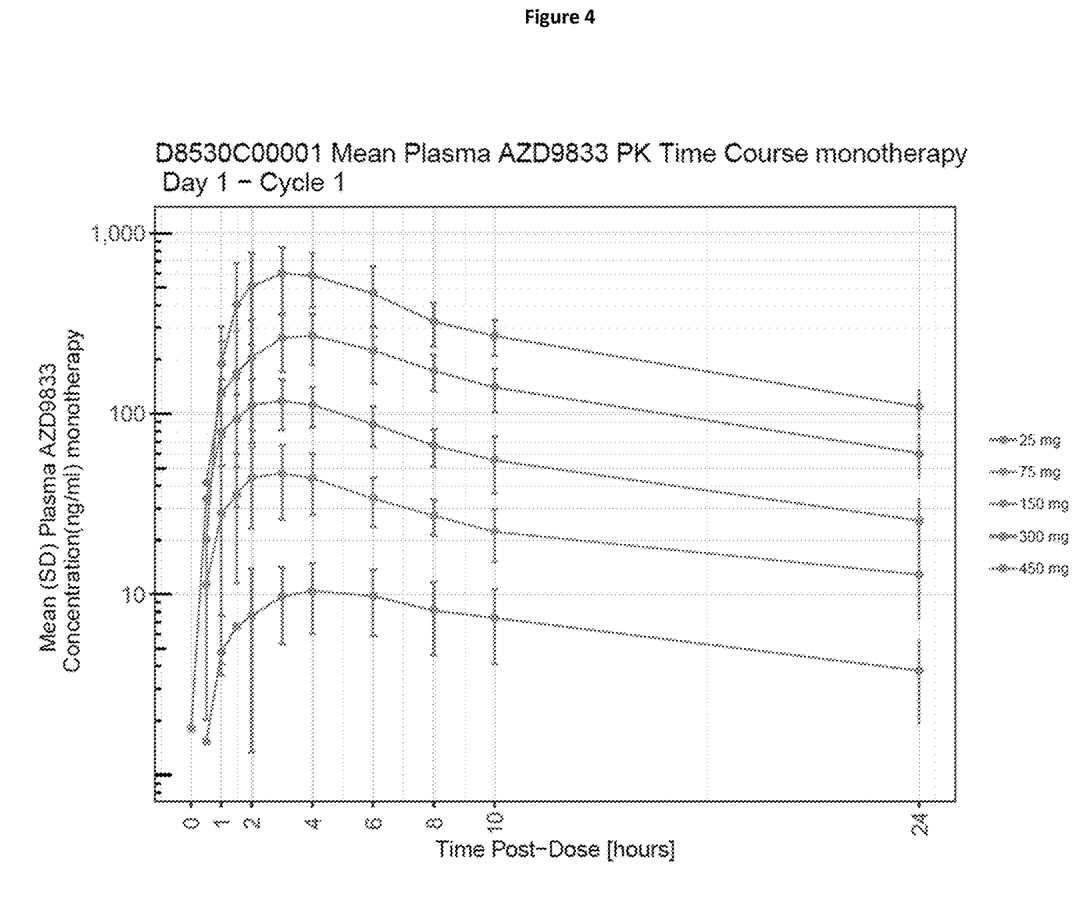
FIG. 4: Mean plasma concentration over time plot following administration of AZD9833 at varying doses.

Part A of the study allow for dose escalation of AZD9833 alone. For these parts, a 'cohort' will constitute all the patients dosed at that particular dose level in the dose escalation scheme as illustrated in FIG. 1. In Part B of the study (expansion), eligible subjects will be randomised to receive selected doses of AZD9833 based on the findings in Part A.

Throughout the study, pre-menopausal subjects will take AZD9833 with a background of a LHRH agonist (see Background Medication).

Part A: Eligible pre- and post-menopausal subjects will receive AZD9833. For initial dosing, the first patient in each cohort will be followed to Day 8 before further patients are allocated to that dose level cohort; see Section 6.1.5.5. When there are sufficient evaluable subjects for a decision regarding dose escalation (between 3 and 6 subjects), the cohort may be optionally expanded to include additional subjects (to have up to 12 evaluable subjects in a cohort) and/or a cohort may be opened at the next dose level. A maximum of 8 dose-level cohorts is anticipated in Part A of the study. Escalation will stop at the MTD/MFD. Part A will include at least 2 subjects with paired tumour biopsies at each dose level.

The dose escalation phase of the study will determine the MTD or MFD of AZD9833 based on the assessment of the safety, tolerability, and PK data collected during the first 28 days of daily dosing. The dose escalation and de-escalation plan for evaluating AZD9833 will follow a Bayesian adaptive design scheme (Neuenschwander et al., Stat Med. 2008, 15:2420), which combines prior expectations about the dose-toxicity relationship and applies the data at the end of each cohort to recommend a dose for the next cohort. Once safety and tolerability have been established following at least 7 days of treatment of the first subject in each dose level cohort, up to 3 additional subjects will be enrolled to ensure at least 3 evaluable subjects at 28 days.

Optional expansions during the dose escalation are included at AZD9833 doses where those doses have a pre-clinically predicted pharmacodynamic effect on ER greater than or equal to fulvestrant, a reasonable standard of care in this disease setting. This will provide an early opportunity for subjects to receive the drug at potentially therapeutic doses and to permit further investigation of the safety, tolerability, and the pharmacologic and biological activity profile of AZD9833. Dose level(s) to be expanded will be based on emerging data and will be approved by the Safety Review Committee (SRC).

The expansion of Part A of the study also provides for the recruitment of at least 2 subjects suitable for paired on-study tumour biopsies to enable a preliminary assessment of tumour pharmacodynamics across a wider range of doses than will be examined in Part B.

Part B: Eligible pre-menopausal (n=12) subjects will receive AZD9833 300 mg (the highest of the three selected dose levels from Part A) and post-menopausal (n=36) subjects will be randomised 1:1:1 to receive either AZD9833 300 mg, AZD9833 150 mg or AZD9833 75 mg. Part B will include at least 5 paired biopsy-evaluable subjects in each of the 4 treatment groups (pre-menopausal dose 300 mg, post-menopausal dose 300 mg, post-menopausal dose 150 mg, post-menopausal dose 75 mg).

Part B will permit further evaluation of the safety profile of AZD9833 in a larger group of post-menopausal subjects at 3 distinct dose levels. The objective of the examination of 3 dose levels is to permit a robust selection of recommended doses for further clinical exploration in future AZD9833 studies, both in the advanced breast cancer setting and, potentially, in the early disease/adjuvant setting. A randomised design is applied to the allocation of 36 subjects to 1 of 3 tolerated dose levels from part A, to facilitate a robust comparison of the safety profile by avoiding allocation or any other potential experimental bias. Part B will also allow for up to 12 pre-menopausal subjects to be allocated to the highest of the 3 doses considered safe and well tolerated in Part A (300 mg).

Part B also includes provision for the recruitment of a subset (n=15 post-menopausal, that is 5 at each dose level and n=5 pre-menopausal at a dose level of 300 mg) of subjects suitable for paired on-study tumour biopsies to enable further assessment of tumour pharmacodynamics.

Study Population: Prospective approval of protocol deviations to recruitment and enrolment criteria, also known as protocol waivers or exemptions, is not permitted. Each subject should meet all of the inclusion criteria and none of the exclusion criteria to be assigned/randomised to AZD9833. Under no circumstances can there be exceptions to this rule. Subjects who do not meet the entry requirements are screen failures.

Enrolled subjects are defined as those who sign informed consent. Treated subjects are those who receive at least 1 dose of AZD9833. In Parts B and D, enrolled subjects are randomised into their treatment group. Randomised subjects are defined as those who undergo randomisation and receive a randomisation number.

Inclusion Criteria: Patients are eligible to be included in the study only if all of the following inclusion criteria and none of the exclusion criteria apply:

1. Provision of signed and dated written informed consent prior to any mandatory study-specific procedures, sampling, and analyses. If a subject declines to participate in any voluntary exploratory research and/or genetic component of the study, there will be no penalty or loss of benefit to the subject and she will not be excluded from other aspects of the study.
2. Aged at least 18 years.
3. Menopausal status as follows:
   (a) Pre-menopausal women must have commenced treatment with an LHRH agonist at least 4 weeks prior to starting AZD9833 and must be willing to continue to receive LHRH agonist therapy for the duration of the study.
   (b) Post-menopausal defined as meeting at least 1 of the following criteria:
      (i) Have undergone a bilateral oophorectomy.
      (ii) Age ≥60 years.
      (iii) Age >50 years and with cessation of regular menses ≥12 months and with an intact uterus in the absence of oral contraception or hormone replacement therapy prior to the diagnosis of breast cancer.
- (iv) Age <60 years and with cessation of regular menses ≥12 months and follicle-stimulating hormone (FSH) and oestradiol levels in the postmenopausal range (utilising ranges from the local laboratory facility).
- (c) Those not meeting the definition for post-menopausal are regarded as pre-menopausal.
4. Histological or cytological confirmation of adenocarcinoma of the breast.
5. Documented positive estrogen receptor status of primary or metastatic tumour tissue, according to the local laboratory parameters and where those laboratory parameters are in accordance with accepted diagnostic guidelines, e.g. American Society of Clinical Oncology/College of American for Pathologists Guideline Recommendations Immunohistochemical Testing of Estrogen and Progesterone Receptors in Breast Cancer (Hammond et. al. 2010). HER2-defined as an immunohistochemistry (IHC) Score 0 or 1+ or negative by in situ hybridisation (ISH; FISH/CISH/SISH); if IHC 2+, ISH negativity is required. Where available, assessment of ER and HER2 status should be based on the most recent tumour biopsy sample.
6. Metastatic disease or locoregionally recurrent disease which is refractory or intolerant to existing therapy (ies) known to provide clinical benefit.
7. Prior chemotherapy, endocrine therapy and other therapy as follows:
    - (a) No more than 2 lines of chemotherapy for advanced disease.
    - (b) Recurrence or progression on at least one line of endocrine therapy in the advanced/metastatic disease setting.
    - (c) There is no limit on the number of lines of prior endocrine therapies.
    - (d) Prior treatment with CDK4/6 inhibitors is permitted.
    A chemotherapy line in advanced disease is an anticancer regimen(s) that contains at least one cytotoxic chemotherapy agent and given for 21 days or longer. If a cytotoxic chemotherapy regimen was discontinued for a reason other than disease progression and lasted less than 21 days, then this regimen does not count as a prior line of chemotherapy. Repeat administration of the same anti-cancer regimen on a separate occasion does not count as a new line of chemotherapy.
8. Metastatic disease or locoregionally recurrent disease which is refractory or intolerant to existing therapy (ies) known to provide clinical benefit.
9. Women of childbearing potential must agree to use one highly effective contraceptive measure (as defined in Section 5.3.1 Contraceptive Measures) from the time of screening until 4 weeks after discontinuing AZD9833, must not be breast feeding, and must have a negative pregnancy test prior to the start of dosing.
10. At least one lesion (measurable and/or non-measurable, as per Response Evaluation Criteria in Solid Tumours version 1.1 [RECIST 1.1] that can be accurately assessed at baseline and is suitable for repeated assessment by computed tomography (CT), magnetic resonance imaging (MRI), or plain X-ray; or clinical examination. Blastic-only lesions in bone are not considered assessable.
11. Eastern Cooperative Oncology Group (ECOG)/World Health Organization (WHO) performance status 0 to 1, with no deterioration over the previous 2 weeks and a minimum life expectancy of 12 weeks.

Exclusion Criteria: Patients must not enter the study if any of the following exclusion criteria are fulfilled:
1. Intervention with any of the following:
    - (a) Any cytotoxic chemotherapy, investigational agents or other anti-cancer drugs for the treatment of advanced breast cancer from a previous treatment regimen or clinical study within 14 days of the first dose of AZD9833.
    - (b) Medications or herbal supplements known to be strong inhibitors/inducers of cytochrome P450 3A4/5 (CYP3A4/5) and sensitive cytochrome P450 2B6 (CYP2B6) substrates (commonly prescribed drugs are listed in Appendix B), or inability to stop use within the washout period as specified in Appendix B prior to receiving the first dose of AZD9833.
    - (c) Drugs that are known to prolong QT and have a known risk of Torsades de Pointes.
    - (d) Radiotherapy with a limited field of radiation for palliation within 1 week of the first dose of AZD9833, with the exception of patients receiving radiation to more than 30% of the bone marrow or a wide field of radiation within 4 weeks of the first dose of AZD9833.
    - (e) Major surgical procedure or significant traumatic injury, as judged by the investigator, within 4 weeks of the first dose of AZD9833, or an anticipated need for major surgery and/or any surgery requiring general anaesthesia during the study.
2. Any unresolved toxicities from prior therapy greater than Common Terminology Criteria for Adverse Events (CTCAE) Grade 1 at the time of starting AZD9833, with the exception of alopecia.
3. Presence of life-threatening metastatic visceral disease, as judged by the investigator, uncontrolled central nervous system (CNS) metastatic disease. Patients with spinal cord compression and/or brain metastases may be enrolled if definitively treated (e.g., surgery or radiotherapy) and stable off steroids for at least 4 weeks prior to start of AZD9833.
4. Any evidence of severe or uncontrolled systemic diseases, including uncontrolled hypertension and active bleeding diatheses, or e.g., infection requiring intravenous antibiotic therapy, which in the investigator's opinion makes it undesirable for the patient to participate in the study or which would jeopardise compliance with the protocol, or active infection (requiring antiviral treatment) including hepatitis B, hepatitis C, and human immunodeficiency virus (HIV).
5. Any of the following cardiac criteria:
    - (a) Mean resting QT interval corrected by Fridericia's formula (QTcF)>470 msec obtained from a triplicate electrocardiogram (ECG).
    - (b) Any clinically important abnormalities in rhythm, conduction, or morphology of resting ECG (ego, complete left bundle branch block, second- and third-degree heart block), or clinically significant sinus pause. Patients with controlled atrial fibrillation can be enrolled.
    - (c) Any factors that increase the risk of QTc prolongation or risk of arrhythmic events such as symptomatic heart failure, hypokalemia, congenital long QT syndrome, immediate family history of long QT syndrome, or unexplained sudden death at <40 years of age. Hypertrophic cardiomyopathy and clinically significant stenotic valve disease.
  (d) Experience of any of the following procedures or conditions in the preceding 6 months: coronary artery bypass graft, angioplasty, vascular stent, myocardial infarction, unstable angina pectoris, congestive heart failure New York Heart Association (NYHA) Grade ≥2, cerebrovascular accident, or transient ischaemic attack.
  (e) Uncontrolled hypertension. Hypertensive patients may be eligible, but blood pressure must be adequately controlled at baseline. Patients may be re-screened regarding the blood pressure requirement.
6. Inadequate bone marrow reserve or organ function as demonstrated by any of the following laboratory values:
  (a) Absolute neutrophil count (ANC)<1.5×10 9/L.
  (b) Platelet count <100×10 9/L.
  (c) Haemoglobin <90 g/L.
  (d) Alanine aminotransferase (ALT)>2.5× the upper limit of normal (ULN).
  (e) Aspartate aminotransferase (AST)>2.5×ULN.
  (f) Total bilirubin (TBL)>1.5×ULN or >3×ULN in the presence of documented Gilbert's Syndrome (unconjugated hyperbilirubinaemia).
  (g) Glomerular filtration rate (GFR)<50 mL/min.
7. Involvement in the planning and conduct of the study.
8. Refractory nausea and vomiting, uncontrolled chronic gastrointestinal (GI) diseases, inability to swallow the formulated product, or previous significant bowel resection that would preclude adequate absorption of AZD9833. History of hypersensitivity to active or inactive excipients of AZD9833 or drugs with a similar chemical structure or class to AZD9833.
9. Judgment by the investigator that the patient should not participate in the study if the patient is unlikely to comply with study procedures, restrictions, and requirements.
10. Male subjects are excluded from this study.

Study Treatments: AZD9833, administered as 25 mg and 100 mg tablets. AZD9833 will be administered as an oral dose, initially once daily. It should be taken in the morning, with or without food, at approximately the same time of day. The SRC may decide to require fed or fasted dosing of AZD9833 (i.e., no food for a minimum of 2 hours prior to and 1 hour after each AZD9833 dose), depending on emerging study data. Alternative dosing frequencies or intermittent schedules of AZD9833 may be initiated following recommendation by the SRC in response to emerging safety, tolerability, and PK data.

Dosing will begin at 75 mg once daily. At each dose level, 1 subject will be exposed and monitored until Day 8; for details. After each dose level during the dose escalation phase of the study, the SRC will evaluate all available safety information. The dose for subsequent cohorts or a decision to stop recruitment will be agreed by the SRC after review of the data from each cohort. Dose escalation and de-escalation will be decided by the SRC. The proposed dose escalation scheme will allow for a doubling in dose with each cohort in principle, e.g. 75 mg, 150 mg, 300 mg, etc. However, alternative or intermediate dose levels may be tested following review of safety data by the SRC.

At least 2 subjects in each dose level in Part A and at least 5 subjects in each cohort in Part B will be selected such that they are suitable for and consent to provide one pre-treatment and one on-treatment paired tumour biopsy sample. In the event that a subject has been selected for provision of paired biopsies, and this becomes clinically unfeasible during the course of their care, the individual cohorts may be expanded by recruiting additional biopsy-eligible subjects until the required number of evaluable biopsy pairs in each cohort have been collected.

There is no maximum duration of treatment, and subjects may continue to receive AZD9833 as long as they are continuing to show clinical benefit, as judged by the investigator. If AZD9833 is discontinued for reasons other than disease progression, the subject must continue tumour assessments until disease progression, or until a further line of anti-cancer therapy is administered.

Dose Limiting Toxicity (DLT): a DLT is defined as an AE or abnormal laboratory value that occurs from the first dose of AZD9833 up to and including Day 28, Cycle 1 (the DLT period) that is assessed as unrelated to disease progression, intercurrent illness, or concomitant medications and that, despite optimal therapeutic intervention, meets any of the following criteria:
  (a) Any death not clearly due to the underlying disease or extraneous causes
  (b) Haematological toxicities as follows (CTCAE):
    (i) Any >Grade 4 haematological toxicity present for more than 4 consecutive days, or requiring blood transfusions, G-CSF, or erythropoietins.
    (ii)>Grade 3 neutropenia of any duration accompanied with fever ≥38.5° C. and/or systemic infection.
    (iii)>Grade 3 thrombocytopenia of any duration with bleeding.
    (iv) Grade 4 thrombocytopenia (regardless of duration or bleeding)
  (c) Any non-haematological toxicity CTCAE >Grade 3 but with the following conditional stipulations:
    (i) Nausea >CTCAE Grade 3 for more than 3 consecutive days despite administration of maximal anti-emetic therapy.
    (ii) Vomiting >CTCAE Grade 3 for more than 3 consecutive days despite administration of maximal anti-emetic therapy.
    (iii) Vomiting >CTCAE Grade 4 (regardless of duration)
    (iv) Diarrhoea >CTCAE Grade 3 for more than 3 consecutive days despite administration of maximal anti-diarrheal therapy.
    (v) Diarrhoea ≥ CTCAE Grade 4 (regardless of duration)
    (vi) CTCAE Grade ≥3 fatigue that persists for more than 4 days.
    (vii) CTCAE Grade ≥3 increase in creatinine.
  (d) Other toxicity:
    (i) QTcF value >500 ms or QTcF prolongation from baseline by 60 ms and >480 ms confirmed on at least 2 separate ECGs.
    (ii)>CTCAE Grade 4 electrocardiogram QT corrected interval prolongation.
    (iii) An increase in serum/plasma AST or ALT ≥3×ULN and concurrent TBL ≥2 ULN.
  (e) Any other toxicity that:
    (i) Is greater than at baseline and is clinically significant and/or unacceptable despite optimal therapeutic intervention, and is judged to be a DLT by the SRC, or
    (ii) Results in a disruption of the dosing schedule of more than 14 days despite optimal therapeutic intervention.

Background medication: Pre-menopausal women must have commenced treatment with an LHRH agonist at least 4 weeks prior to starting AZD9833 and continue LHRH agonist therapy throughout the duration of the study.

Efficacy Assessment: Anti-tumour activity will be evaluated using RECIST 1.1 by investigator assessments. Baseline tumour assessments should encompass all areas of known predilection for metastases in the disease under evaluation and should additionally investigate areas that may be involved based on signs and symptoms of individual subjects. Baseline assessments should be performed no more than 28 days before the start of AZD9833, ideally, as close as possible to the start of AZD9833. The methods of assessment used at baseline should be used at each subsequent assessment during treatment and follow-up part of the study. Any other sites at which new disease is suspected should also be appropriately imaged.

If an unscheduled assessment is performed and the subject has not progressed, every attempt should be made to perform subsequent assessments at the scheduled visits while the subject remains on AZD9833 or until she has progressed. Categorisation of objective tumour response assessment will be based on the RECIST 1.1 guidelines for response: complete response (CR), partial response (PR), stable disease (SD), and progression of disease (PD). For subjects who only have non-measurable disease at baseline, categorisation of objective tumour response assessment will be based on the RECIST 1.1 guidelines for response for non-target lesions (NTLs): CR, PD, and non-CR/non PD. If the investigator is unsure whether progression has occurred, particularly with response to NTLs or the appearance of a new lesion, it is advisable to continue AZD9833 and reassess the subject's status at the next scheduled assessment, or sooner if clinically indicated. To achieve 'unequivocal progression' on the basis of non-target disease, there must be an overall level of substantial worsening in non-target disease such that, even in presence of SD or PR in the target disease, the overall tumour burden has increased sufficiently to merit discontinuation of therapy. A modest increase in the size of one or more NTLs is usually not sufficient to qualify for unequivocal disease progression status.

Safety and Clinical Assessments: The safety and tolerability of AZD9833 is the primary objective of this study. Related outcome measures are DLTs, AEs/SAEs, vital signs, clinical chemistry/haematology, and ECGs.

Clinical Safety Laboratory Assessments: Clinical chemistry, haematology, and urinalysis and coagulation will be performed at a local laboratory at or near to the investigator study site. Sample tubes and sample sizes may vary depending on laboratory method used and routine practice at the study site.

Pharmacokinetics: The characterisation of the pharmacokinetics of single and multiple doses of AZD9833 is a secondary objective of this study. Any residual sample remaining after PK analysis has been performed may be used to identify, characterise, and establish the concentration of AZD9833 metabolites and drug-related products in plasma, and/or to conduct exploratory biomarker research. Analysis of AZD9833 in plasma and urine will be performed using appropriate bioanalytical methods. Full details of the analytical methods used will be described in separate bioanalytical reports.

All samples within the known stability of the analytes of interest at the time of receipt by the bioanalytical laboratory will be analysed. In addition, the PK samples may be subjected to further analyses to identify, characterise, and establish the concentration of metabolites in plasma. Any results from such analyses will be reported separately from the clinical study report. Incurred sample reproducibility analysis, if any, will be performed with the bioanalysis of the test samples. The results from the evaluation will not be reported in the clinical study report but, separately, in a bioanalytical report.

Pharmacodynamics: Pharmacodynamic measurements will be made on a number of biomarkers (e.g., optional tumour biopsies, plasma ctDNA, CTC, and archival tumour tissue). Biological samples (archival tumour tissue, mandatory and optional biopsies where applicable) will be collected for the analysis of tumour DNA as an exploratory objective in this study. A 2-mL blood sample for DNA isolation will be collected prior to administration of the first dose of AZD9833 from subjects who have consented to participate in the genetic analysis component of this study. If for any reason the sample is not drawn prior to dosing, it may be taken at any visit until the last study visit. Only one sample for genetic research should be collected per subject during the study. Participation is optional. Subjects who do not wish to participate in the genetic research may still participate in the study.

Biomarkers: The following samples for exploratory biomarker research are optional or required, as indicated, and will be collected from the appropriate subjects.

In Part A, paired tumour biopsy samples will be taken from at least 2 subjects at each dose level. In Part B, these biopsies will be taken from at least 5 post-menopausal subjects at each AZD9833 dose level, 300 mg, 150 mg and 75 mg and at least 5 from pre-menopausal subjects at 300 mg. If subjects are willing to participate in this part of the study, they will sign a biopsy-specific written informed consent. Paired tumour biopsies will be obtained from subjects with accessible tumours who have consented to biopsies. Accessible lesions are defined as tumour lesions that are biopsiable, and amenable to repeat biopsy.

The pre-treatment biopsy will be taken during screening as close as possible to starting treatment. The on-treatment sample should be taken on Day 1 (+7 days) of Cycle 2 but can be taken outside this time window, if agreed with AstraZeneca. A further (optional) tumour biopsy should also be taken on disease progression or at the end of treatment. The biomarkers to be investigated using tumour samples may include, but will not necessarily be limited to: ER, PgR, Ki67, genomic/genetic alterations, and other ER-regulated gene expression. Where feasible, collection of a tumour biopsy at disease progression is encouraged. This sample will be used to investigate changes in pathway signalling and potential mechanisms of resistance (i.e., genetic alterations or evidence of alternative pathway activation).

Formalin-fixed archival tumour tissue embedded in paraffin blocks are to be retrieved for all subjects, where available. If baseline biopsy samples can also be collected, retrieval of the archival diagnostic tumour material is still required to provide data on how the tumour has evolved since diagnosis. The archival samples can be derived from the primary tumour and/or metastatic site and, where possible, the most recently acquired archival sample is required. Freshly prepared unstained slides from the archival tumour block are accepted, if tumour blocks cannot be submitted. From submitted archival tumour blocks, cores may be removed to construct tissue microarrays for later biomarker analysis. The remaining part of the tumour block may be returned to the institution.

One 2-mL blood sample will be taken at each of the timepoints, for cancer antigen CA15-assessment.

Blood samples will be taken at each of the timepoints. These samples will be taken to obtain a preliminary assessment of AZD9833 activity in the tumour by evaluation of pharmacodynamic biomarker changes, which may include but are not limited to total counts, and expression levels of ER, Ki67 protein, and ER-regulated genes.

One 10-mL blood sample will be taken at the timepoints below to provide 2 samples of plasma and one sample of serum per timepoint. The samples will be collected and stored to permit retrospective exploratory biomarker analysis and will be analysed for a range of oncology biomarkers that may correlate with drug response.

Two 2.5-mL whole blood samples will be collected in PAXgene tubes for RNA and microRNA/RNA samples preparation. Analysis of RNA may be conducted to generate hypotheses associated with the mechanisms of action of the molecule evaluated in the study and to potentially identify changes in gene expression that correlate with treatment response.

One 20-mL blood sample will be taken at screening, and 10-mL blood sample will be taken at all of the other timepoints to provide plasma. It will be used for the extraction and analysis of ctDNA for the analysis of predictive and pharmacodynamic biomarkers to interrogate changes in genetic alterations and potential mechanisms of resistance.

Clinical Trial Results

A clinical trial according to the above protocol was carried out using 60 patients. The results can be summarised as follows.

60 patients were treated (median age 61 (range 39-79)) across five doses; 25 mg QD n=12, 75 mg QD n=12, 150 mg QD n=13, 300 mg QD n=13, 50 mg QD n=10. AZD9833 exposure was dose proportional after multiple doses, with a median terminal t1/2 of 12 h.

Treatment-related AEs experienced by >10% of patients were visual disturbances (53%; 91% G1, 6% G2, 3% G3), bradycardia/sinus bradycardia (45%; 93% G1, 7% G2), nausea (18%; 46% G1, 55% G2), fatigue (13%; 38% G1, 63% G2), dizziness (10%; 83% G1, 17% G3) vomiting (10%; 50% G1, 33% G2, 17% G3), and asthenia (10%; 67% G1, 33% G2). Three patients experienced DLTs: G3 QTcF prolongation (300 mg); G3 vomiting (450 mg); and a combination of G2 visual disturbance, G2 headache and G2 gait disturbance (450 mg). DLT cases were managed with dose reduction. No G4 or 5 AEs were reported. None of the observed AEs were deemed to be clinically relevant.

Efficacy data are presented in the table below; objective response rate (ORR) and clinical benefit rate (CBR) at 24 weeks:

ER signalling pathway modulation was observed in all dose cohorts. In patients where clinical responses occurred and paired biopsies obtained, 98% reduction in Ki67 was measured.

These data show that AZD9833 has an encouraging efficacy and dose-dependent safety profile. Evidence of clinical benefit and target engagement was observed at all dose levels in women with ER+ABC, including patients pre-treated with CDK4/6 inhibitors and fulvestrant, and those with ESR1 mutations.

The invention claimed is:

1. A method of treating ER-positive HER2-negative breast cancer in a human patient in need of such treatment, comprising orally administering to the patient a compound, or a pharmaceutically acceptable salt thereof, once daily at a dose of 75 mg, wherein the compound is N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f] isoquinolin-6-yl) pyridin-3-amine.

2. The method of claim 1, wherein the compound is administered as a single dose unit or as multiple dose units.

3. The method of claim 1, wherein the compound is administered as a single tablet.

4. The method of claim 1, wherein the compound is administered in combination with a further anti-cancer therapy.

5. The method of claim 1, wherein the cancer is ER-positive HER2-negative advanced breast cancer.

6. The method of claim 1, wherein the compound is administered to a pre- or post-menopausal woman.

7. The method of claim 1, wherein the cancer has previously been treated with one or more endocrine therapies and no more than two prior chemotherapies for ER-positive HER2-negative advanced breast cancer.

8. The method of claim 1, wherein the compound is administered to a patient whose cancer is resistant to non-steroidal aromatase inhibitors.

9. The method of claim 1, wherein the dose achieves a mean peak blood plasma concentration in the patient between 10 ng/ml and 1000 ng/mL.

10. The method of claim 1, wherein the dose achieves a median terminal half-life in the patient between 8 hours and 14 hours.

11. The method of claim 1, wherein the dose achieves a median terminal half-life in the patient of 12 hours.

12. The method of claim 1, wherein the dose achieves an objective response rate in the patient of at least 10%.

TABLE 5

|  | 25 mg (n = 12) | 75 mg (n = 12) | 150 mg (n = 13) | 300 mg (n = 13) | 450 mg (n = 10) | Total (n = 60) |
| --- | --- | --- | --- | --- | --- | --- |
| ORR (%) | 1/9 (11.1) | 1/7 (14.3) | 2/11 (18.2) | 2/10 (20.0) | 1/6 (16.7) | 7/43 (16.3) |
| CBR (%) | 4/12 (33.3) | 8/12 (66.7) | 4/13 (30.8) | 3/11 (27.3) | 3/4 (75.0) | 22/52 (42.3) |

13. The method of claim 1, wherein the dose does not cause any serious side-effects in the patient.

\* \* \* \* \*